US011694788B2

(12) United States Patent
Paffel et al.

(10) Patent No.: US 11,694,788 B2
(45) Date of Patent: Jul. 4, 2023

(54) HEALTHCARE PROTOCOLS FOR USE WITH A DISTRIBUTED LEDGER

(71) Applicant: Medtronic, Inc., Minneapolis, MN (US)

(72) Inventors: Timothy D. Paffel, Shafer, MN (US); Michael D. Ryan, Blaine, MN (US); Jake Schutz, Blaine, MN (US); Tracy E. Kootsikas, Minneapolis, MN (US); Kurt R. Smith, Boulder, CO (US)

(73) Assignee: Medtronic, Inc., Minneapolis, MN (US)

( * ) Notice: Subject to any disclaimer, the term of this patent is extended or adjusted under 35 U.S.C. 154(b) by 719 days.

(21) Appl. No.: 16/425,286

(22) Filed: May 29, 2019

(65) Prior Publication Data

US 2019/0371457 A1 Dec. 5, 2019

Related U.S. Application Data

(60) Provisional application No. 62/677,436, filed on May 29, 2018.

(51) Int. Cl.
| | |
|---|---|
| *G16H 40/20* | (2018.01) |
| *G06F 16/27* | (2019.01) |
| *G16H 70/20* | (2018.01) |
| *H04L 9/32* | (2006.01) |
| *G16H 10/60* | (2018.01) |
| *H04L 9/00* | (2022.01) |

(52) U.S. Cl.
CPC ............ *G16H 40/20* (2018.01); *G06F 16/27* (2019.01); *G16H 10/60* (2018.01); *G16H 70/20* (2018.01); *H04L 9/3242* (2013.01); *H04L 9/50* (2022.05)

(58) Field of Classification Search
CPC ........ G16H 40/20; G16H 10/60; G16H 70/20; G06F 16/27; H04L 9/3242
See application file for complete search history.

(56) References Cited

U.S. PATENT DOCUMENTS

| | | |
|---|---|---|
| 9,135,787 B1 | 9/2015 | Russell et al. |
| 9,794,074 B2 | 10/2017 | Toll et al. |
| 9,818,092 B2 | 11/2017 | Pennanen |
| 9,836,908 B2 | 12/2017 | Spanos et al. |
| 9,853,977 B1 | 12/2017 | Laucius et al. |
| 2015/0332283 A1 | 11/2015 | Witchey |
| 2016/0117471 A1 | 4/2016 | Belt et al. |
| 2016/0260169 A1* | 9/2016 | Arnold ................ G06Q 20/023 |
| 2016/0342989 A1 | 11/2016 | Davis |
| 2017/0039330 A1 | 2/2017 | Tanner, Jr. et al. |
| 2017/0161439 A1 | 6/2017 | Raduchel et al. |
| 2017/0300627 A1* | 10/2017 | Giordano ............ G06F 21/6245 |
| 2018/0227119 A1* | 8/2018 | Bibera ................... G06Q 40/04 |

OTHER PUBLICATIONS

Peterson et al., "A Blockchain-Based Approach to Health Information Exchange Networks," 2016, 10 pages.

* cited by examiner

*Primary Examiner* — John P Go
(74) *Attorney, Agent, or Firm* — Mueting Raasch Group

(57) ABSTRACT

Systems and methods may use healthcare protocols for use with distributed ledger technology. The healthcare protocols may be used to, among other things, classify event data items as distributed ledger data items such that record of such classified event data items may be stored in a distributed ledger. Further, the healthcare protocols may be modified over time, and record of such modifications may also be stored in a distributed ledger.

36 Claims, 8 Drawing Sheets

HEALTHCARE PROTOCOLS FOR USE WITH A DISTRIBUTED LEDGER

This application claims the benefit of U.S. Provisional Application Ser. No. 62/677,436, filed May 29, 2018, the disclosure of which is incorporated by reference herein in its entirety.

The present invention relates generally to systems and methods using healthcare protocols for use with a distributed ledger.

Healthcare environments often has many different systems of record that may contain relevant information regarding patients and data regarding the health of patients. For a healthcare provider to "make a decision" about a patient's appropriate care pathway, access to these multiple systems of record may not be possible, at least in a timely manner. In addition, since these systems are under the control of various organizations, the ability to "reconstruct" the information that was available and may have been presented to the healthcare provider at the time of the decision can be difficult to reconstruct.

SUMMARY

The illustrative systems and methods described herein may be described as providing an immutable record that captures the state of attributes (e.g., digital information) used to guide decisions made during the care of a patient. For example, the illustrative systems and methods may generate, or cooperate with other systems and methods to generate, an immutable record of linked attributes (referred to in some examples as the "payload") used by a care professional or a care support system for a decision being made. In one example, ordering labs for a patient may be considered a healthcare event, which may include one or more event data items that could be made immutable by using the illustrative systems and methods described herein. This immutable record can be used for further monitoring, evaluation, and analysis to help prove and/or verify desired healthcare outcomes. Further, this style of attribution may be described as enabling a trusted record to be used as a feedback loop in the illustrative systems and methods for review, improvement, and adaptation of health care protocols.

The illustrative systems and methods may further be described as an amalgamation of computer resources (e.g., information technology systems) that coordinate, aggregate, and record the attributions and key pieces of information (e.g., the payload) used to make health care decisions as transactions in a distributed ledger (e.g., an immutable record). The transactions may be packaged and recorded in off-ledger storage (e.g., data storage not associated with a distributed ledger), and made immutable by a distributed ledger technology (e.g., blockchain). In one or more embodiments, a recorded transaction may be a link to decisions made and a reference to an off-ledger copy of these attributions (e.g., the payload) for later review, if desired.

Various illustrative embodiments are directed toward solving technical issues with using distributed ledger for transactions where, for example, the importance of different data items of healthcare events varies over time (e.g., as protocols are changed, as patient conditions change, etc.) and between different patients (e.g., based upon patient conditions, demographics, etc.). In certain illustrative embodiments, these issues can be addressed by identifying the data items that according healthcare protocols should be submitted to and made immutable by a distributed ledger. In various illustrative embodiments, data items may be classified as distributed ledger data items based on healthcare protocols as well as other factors such as patient conditions and demographics.

Further, various illustrative embodiments are directed toward solving technical issues with using distributed ledger for transactions where, for example, the healthcare protocols (which are used to determine what data items of healthcare events should be submitted to and made immutable by a distributed ledger) change over time due to, e.g., healthcare outcomes, new research, etc. In certain illustrative embodiments, these healthcare protocol changes may be classified themselves as distributed ledger data items so as to be submitted to and made immutable by a distributed ledger. In this way, changes to how healthcare events may be verifiable using the distributed ledger.

One illustrative system for use with a plurality of participants (e.g., one or more of patient monitoring apparatus, treatment data sources, payor systems, healthcare attribution coordinator systems, and provider systems) and a distributed ledger may include, among other things, a computing apparatus comprising one or more processors. The computing apparatus may be configured to receive a healthcare event associated with a patient from one or more participants, the healthcare event comprising one or more event data items, identify, for the received healthcare event, one or more healthcare protocols associated with the patient (e.g., the one or more healthcare protocols associated with the patient may correspond to health conditions of the patient) corresponding to the received healthcare event, and classify, based on the identified one or more healthcare protocols, one or more event data items of the received healthcare event as distributed ledger data items. For the one or more event data items of the received healthcare event classified as distributed ledger data items, the computing apparatus may be further configured to generate, one or more distributed ledger transaction requests, and then submit the one or more distributed ledger transaction requests to the distributed ledger.

One illustrative method for use with a plurality of participants and a distributed ledger may include receiving a healthcare event associated with a patient from one or more participants, the healthcare event comprising one or more event data items, identifying, for the received healthcare event, one or more healthcare protocols associated with the patient corresponding to the received healthcare event, classifying, based on the identified one or more healthcare protocols, one or more event data items of the received healthcare event as distributed ledger data items, generating, for the one or more event data items of the received healthcare event classified as distributed ledger data items, one or more distributed ledger transaction requests, and submitting the one or more distributed ledger transaction requests to the distributed ledger.

One illustrative system for use with a plurality of participants and a distributed ledger may include, among other thing, a computing apparatus comprising one or more processors. The computing apparatus may be configured to: provide a plurality of treatment protocols used to classify event data items of healthcare events as distributed ledger data items to be stored on the distributed ledger; modify the one or more healthcare protocols; generate, for the modified one or more healthcare protocols, one or more distributed ledger transaction requests; and submit the one or more distributed ledger transaction requests to the distributed ledger.

One illustrative method for use with a plurality of participants and a distributed ledger may include providing a plurality of treatment protocols used to classify event data items of healthcare events as distributed ledger data items to be stored on the distributed ledger, modifying the one or more healthcare protocols, generating, for the modified one or more healthcare protocols, one or more distributed ledger transaction requests, and submitting the one or more distributed ledger transaction requests to the distributed ledger.

In one or more embodiments, the healthcare event may include a provider decision event regarding the patient. Further, for example, the provider decision event may include a drug dosage decision and the one or more event data items of the drug dosage decision may include the drug dosage and one or more health factors of the patient related to the drug dosage.

In one or more embodiments, the healthcare event may include a testing event regarding the patient, and the one or more event data items of the testing event may include laboratory test results.

In one or more embodiments, the computing apparatus may be further configured to execute or the method may further include allowing a user to assign one or more healthcare protocols to the patient.

In one or more embodiments, the computing apparatus may be further configured to execute or the method may further include modifying the one or more healthcare protocols and generating, for the modified one or more healthcare protocols, one or more distributed ledger transaction requests. For example, modifying the one or more healthcare protocols may include modifying the one or more event data items to be classified as distributed ledger data items according to the one or more healthcare protocols. Further, for example, modifying the one or more event data items to be classified as distributed ledger data items according to the one or more healthcare protocols may include allowing a user to modify the one or more event data items to be classified as distributed ledger data items according to the one or more healthcare protocols. Still further, for example, modifying the one or more healthcare protocols may include modifying the one or more healthcare protocols based on one or patient outcomes using the one or more healthcare protocols.

In one or more embodiments, the system may further include off-ledger storage operably coupled to the computing apparatus, and the computing apparatus may be further configured to execute or the method may further comprise storing the one or more event data items of the received healthcare event on the off-ledger storage and determining whether the stored one or more event data items of the received healthcare event on the off-ledger storage that had been classified as distributed ledger items have been modified based the distributed ledger.

In one or more embodiments, generating, for the one or more event data items of the received healthcare event classified as distributed ledger data items, one or more distributed ledger transaction requests may include packaging the one or more event data items of the received healthcare event classified as distributed ledger data items into a payload, assigning an identifier to the payload, assigning a time stamp to the payload, generating a keyed-hash message authentication code for the payload, and transmitting the keyed-hash message authentication code to the distributed ledger.

The above summary of the present invention is not intended to describe each embodiment or every implementation of the present invention. Advantages, together with a more complete understanding of the invention, will become apparent and appreciated by referring to the following detailed description and claims taken in conjunction with the accompanying drawings.

DETAILED DESCRIPTION OF ILLUSTRATIVE EMBODIMENTS

Figure 1:
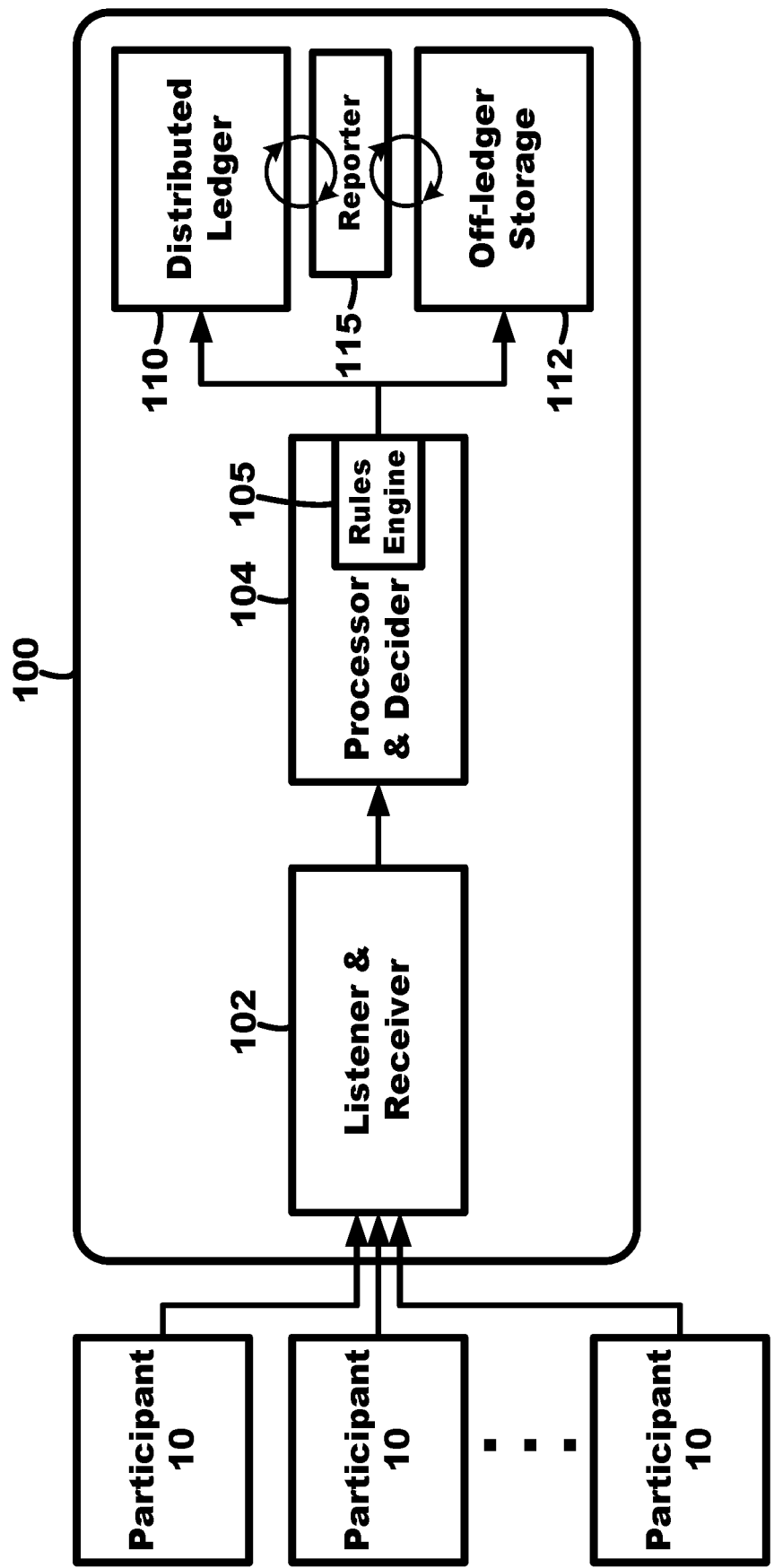
FIG. 1 is a block diagram of an illustrative system for use with healthcare protocols and a distributed ledger.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Illustrative systems and methods shall be described with reference to FIGS. 1-8. It will be apparent to one skilled in the art that elements or processes from one embodiment may be used in combination with elements or processes of the other embodiments, and that the possible embodiments of such systems and methods using combinations of features set forth herein is not limited to the specific embodiments shown in the Figures and/or described herein. Further, it will be recognized that timing of the processes may be modified but still fall within the scope of the present disclosure, although certain timings may be advantageous over others.

The illustrative systems and methods disclosed herein may be generally described as using and modifying healthcare protocols for the selection, or filtering, of data related to healthcare events from a plurality of participants that is made to be immutable using distributed ledger technology. A patient may have one or more healthcare protocols associated thereto based on one or more health conditions of the patient. For example, if a patient has lung cancer, a lung cancer healthcare protocol may be assigned to, or associated with, the patient. Over the course of treatment of the patient, various participants such as health care providers, patient monitoring services, and other data sources may provide data items associated with one or more healthcare events that may be identified as being important and other data items data items associated with one or more healthcare events that may be not identified as being important. The more important data items may be identified using the healthcare protocols associated with the patient and classified as distributed ledger data items. The illustrative systems and methods may store the data items, and records may be generated and stored within a distributed ledger for the distributed ledger data items (e.g., such that the distributed ledger data items may be made immutable). More specifically, in an attribution use case, a medical transaction (e.g., a decision) may be made at a specific time, and the illustrative systems and methods may be able to provide the ability to make the medical transaction trusted, traceable, and immutable; in other words, an accountable record of the existence of the medical transaction may be created.

Thus, for example, a clinician may make care decisions, and data related to the care decisions may be packaged according to one or more healthcare protocols, transacted into a distributed ledger (e.g., blockchain), and a copy of the data stored on off-ledger storage. The data may be stored for later use, and when the data is requested (e.g., to assess prior care decisions), the data may be verified using the distributed ledger.

An illustrative system 100 for use with healthcare protocols and a distributed ledger is depicted in FIG. 1. In some embodiments, the system 100 may be described as a health attribution system. The system 100 may be operably coupled to one or more, or a plurality, of participants, or data sources, 10. The operable coupling between the system 100 and the participants 10 may include any one or more wired or wireless networks for the transfer of data (such as, e.g., the internet).

In one or more embodiments, the participants 10 may be any source of healthcare data regarding patients. For example, the participants 10 may include provider systems (e.g., clinics, hospital, labs, etc.), remote and local patient monitoring systems (e.g., medical device data, etc.), treatment data sources (e.g., practice standard updates, machine learning, clinician input, etc.), and payor systems.

In one or more embodiments, it may be described that the illustrative system 100 may access, integrate with, and assume data from the participants, or clinical data sources, 10 that may be needed to capture decisions about patients' (e.g., patients under the care of an entity) care pathways. The participants may be referred as "agents" in some embodiments, and these agents can be human (e.g., human input into an information technology system, human input into an analog system, human feedback via survey, etc.), information technology (IT) systems (e.g., electronic medical record systems, mobile applications, machine learning systems, artificial intelligence systems, augmented reality systems, robots, etc.), and/or hybrids of both human and IT systems.

Integration to or with these participants 10 may leverage "industry best" practices to define the data interoperability methods, and the types of data collected. For example, an illustrative participant 10 may provide discharge data (e.g., from a clinic's electronic medical record (EMR) system to get admission, discharge, and transfers (ADT) data (e.g., using the HL7 standard)). More participant examples can include population health systems (which, e.g., could be used to risk stratify a cohort), care management systems (which, e.g., could be used to monitor cohorts), care pathway systems (which, e.g., could be used to define a healthcare protocol), and any other systems that may provide data related to the care of a patient.

The system 100 may be described as being a computer apparatus including one or more processors that are configured to provide, or perform, the functionality and processes described herein. It is to be understood that the disclosure herein is not to be limited by the type or configuration of computing apparatus. Instead, it is contemplated that any computing apparatus or amalgamation of computing resources may be used with the illustrative functionality and processes described herein.

Furthermore, the techniques described in this disclosure, including those attributed to the system 100 and/or various constituent components, may be implemented, at least in part, in hardware, software, firmware, or any combination thereof. For example, various aspects of the techniques may be implemented within processing circuitry and/or one or more processors including one or more microprocessors, DSPs, ASICs, FPGAs, or any other equivalent integrated or discrete logic circuitry, as well as any combinations of such components, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the illustrative systems and methods described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The system 100, as shown in FIG. 1, may be described as a combination of interoperable modules, which may be separate software or hardware in some implementations. More specifically, in this example, the system 100 may include a listener and receiver 102, a processor and decider 104 that may further include, or use, a rules engine 105, a distributed ledger 110, off-ledger storage 112, and a reporter 115. Arrows extend between these various modules, or processes, of system 100 to indicate a usage flow of data through the system 100. Further, the arrows may utilize industry standards used by IT systems to connect, extract, and transport data within and outside of the system 100.

The listener and receiver 102 may be described as one or more systems or modules that connects the system 100 to the participants 10, ingests data from the participants 10, and classifies new or existing patients. For example, classifying new patients may include enrollment, registration, and unique identifier generation for the new patients. Further, the listener and receiver 10 may be configured to forward data to processor and decider 104.

The "listener" of the listener and receiver 102 may function to maintain a connection to participants, or data sources, 10 to ingest the data therefrom, and to parse the consumed data to be used by "receiver" of the listener and receiver 102. The "receiver" of the listener and receiver 102 may be described as using predefined events (e.g., ADT data, other messages, etc.) and being configured to determine if patients are enrolled in the system 100. If a patient is enrolled, the "receiver" may tag data with the patient's unique identifier to associate the data with the patient, and then forward the tagged data to the processor and decider 104. In other words, if a patient is already enrolled, the data related to the patient will be tagged with the unique identifier of the patient.

If a patient is not enrolled, the "receiver" may generate a unique identifier in the system 100 for this new patient and complete registration of this new patient including logging such action. In other words, a unique identifier may be generated for this new patient so as to identify them in the system 100 for further processing (e.g., analysis performed, and service probability defined which could make them become enrolled). Further, the "receiver" may remain ready to receive new patient triggers, which, for example, may lead to the identification of more healthcare protocols to be associated with the patient. For instance, if patient recently entered a lung cancer study, the patient could also be entered in a hypertension pathway.

The processor and decider 104 may be described as one or more systems, or modules, that assumes, or receives, the tagged patient data from the listener and receiver 102 to be processed. For example, the processor and decider 104 may generally organize the data, check the data against various rules, and forward the results to proper downstream services. The "processor" of the processor and decider 104 may serialize the received data, and then qualify and prepare (e.g., format, type, etc.) the data so that its results can be forwarded to the "decider" of the processor and decider 104. The "decider" of the processor and decider 104 may be configured to apply the rules engine 105 to the data to resolve what to do next with the content of the data.

The rules engine 104 may use, or leverage, a plurality of healthcare protocols. One or more of the healthcare protocols may be assigned to a patient, and the rules engines 105 may be used to consult the healthcare protocols associated with a patient whose data was received by the system 100 from the participants 10. The "decider" of the processor and decider 104 and the rules engine 105 may be described as using the healthcare protocols to make decisions regarding the received healthcare data.

More specifically, the "decider" of the processor and decider 104 may decide, or determine, whether or not the data should be recorded in the distributed ledger 110 as will be further described herein with reference to FIGS. 2-5. In one or more embodiments, the rules engine 104 may be further described as being a configurable interface that maps to a defined care management system and leverages existing healthcare protocol elements from the participants, or source agents, 10 to provide a measurable set of time stamps to verify improvement trends/outcomes.

In other words, the listener and receiver 102 and the processor and decider 104 may be operate together to receive healthcare data from the participants 10, identify a patient associated with the healthcare data, identify healthcare protocols associated with the patient, and make decisions regarding the healthcare data based on the identified healthcare protocols associated with the patient.

The distributed ledger, or distributed ledger technology (DLT) recorder, 110 may be any set of IT resources (e.g., servers, clients, applications, etc.) configured for providing, or operable to provide, immutable records related to healthcare events, event data items of healthcare events, and changes, or modifications, of healthcare protocols. The distributed ledger 110, in one or more embodiments, may be an implementation of a blockchain set of technologies (e.g., ETHEREUM, HYPERLEDGER, RIPPLE, etc.) for the purposes of recording immutable records (e.g., transactions on the distributed ledger, or blockchain, are immutable).

In one or more embodiments, the distributed ledger 110 may be described as being seamlessly integrated with devices/sensors on a trusted network, which may depend on the distributed ledger technology's deployment model. For example, in a private DLT, the remaining portions of the system 100 may be defined so as to participate as sources to the distributed ledger 110.

In one or more embodiments, the distributed ledger 110 may be described as being able to host the mechanisms for making an immutable record of transactions by way of, or using, smart contracts (e.g., a one-to-one relationship of a transaction to a contract may be used). A smart contract may be described as a Turing complete, computerized transactional procedure that executes, via computer code, the terms of a contract. The smart contracts may be coded to ensure that no data contained within the smart contracts can be modified/written once "mined." Further, as described herein, these transactions being made in the immutable record of the distributed ledger 110 may represent a decision being made such as, e.g., a healthcare event that later may be determined to be a critical event (which may be reviewed, or used, at a later time to help measure outcomes).

The off-ledger storage 112 may be described as any data storage apparatus or system that is configured to store data that is processed by the system 100 such as healthcare events, event data items associated with healthcare events, healthcare protocols, changes to healthcare protocols, patient information, etc. It is to be understood that the off-ledger storage 112 may include at least some data that does not have transaction records recorded in the distributed ledger 110 so as to have been made immutable. In other words, the off-ledger storage 112 may include data that is not made immutable by the distributed ledger 110. Thus, the off-ledger storage 112 is described as being "off" the distributed ledger 110. Nonetheless, the off-ledger storage 112 may store data that has had transaction records recorded in the distributed ledger 110, and thus, made immutable by the distributed ledger 110.

In one or more embodiments, the off-ledger storage 112 may be a set of database storage technologies (e.g., MONGODB, CASANDRA, COUCHDB, RMDBS, etc.) used to store a copy of data from the participants 10. Further, in one or more embodiments, the data stored in the off-ledger storage 112 may be categorized, or grouped, in two types of data, and stored in two different collections or tables. The first collection may include "payloads" of data collected from the participants 10 that were determined by the processor and decider 104 and the rules engine 105 to be recorded in the distributed ledger 110. The second collection may include "payloads" of data collected from the participants 10 that were determined by the processor and decider 104 and the rules engine 105 to not be recorded in the distributed ledger 110. For example, such data may include data captured for other monitoring purposes and data analysis (e.g., basic reporting, artificial intelligence, machine learning, etc. as feedback to care pathways). Thus, the off-ledger storage 112 may be described as any storage for storing data that has not been recorded on, or hashed to, the distributed ledger 110 and for storing data (e.g., raw data payloads) that has been recorded on, or hashed to, the distributed ledger 110.

The reporter 115 may interface with both of the distributed ledger 110 and the off-ledger storage 112 to perform various actions using the distributed ledger 110 and the off-ledger storage 112. For example, the reporter 115, which may include a set of application protocol interfaces such that other modules may interface therewith, may be used to verify transactions on the distributed ledger 110 with the data stored on the off-ledger storage 112 or with data from any participant 10. Further, for example, the reporter 115 may be configured to monitor the performance of various healthcare protocols by analyzing data in the distributed ledger 110 and the off-ledger storage 112. For instance, the reporter 115 may determine whether or not to modify a healthcare protocol based on data in the distributed ledger 110 and the off-ledger storage 112, which is further described herein with respect to FIGS. 7-8. The reporter 115 may further be described as a dynamic component that may change over time due to its ability to feed information back into the overall system 100.

In one or more embodiments, the reporter 115 may include application protocol interfaces that provide metrics on a number of transactions performed in the last second, hour, day, month, etc., a number of smart contracts contained within the distributed ledger 110, originating source data verification methods, a size of data being stored in the off-ledger storage 112, a number of common decision patterns contained in the repositories, and data extraction methods to place data into an outcomes engine.

It is to be understood that the system 100 of FIG. 1 is only one illustrative embodiment, and other systems including various modules, or components, are contemplated in this disclosure. Further, illustrative methods including a plurality of processes and steps are described herein with respect to FIGS. 2-8. It is to be understood that each of such processes and steps described herein with respect to FIGS. 2-8 may be performed by one or more modules, or components, of the illustrative system 100. Further, other systems including various modules, or components, may be configured in a different fashion than depicted system 100 to perform the processes and steps described herein with respect to FIGS. 2-8.

Figure 2:
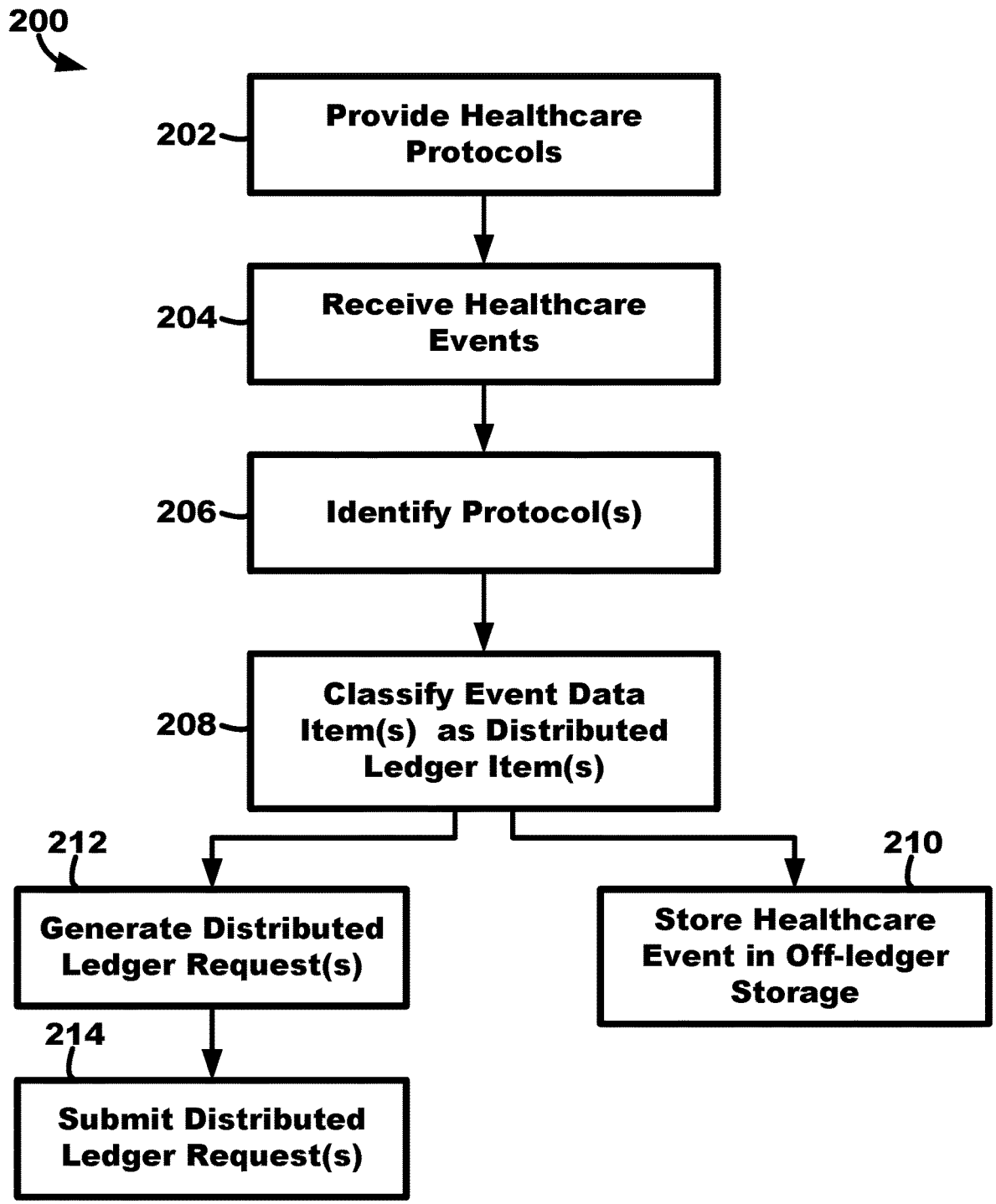
FIG. 2 is a flow diagram of an illustrative method of using healthcare protocols to classify event data items as distributed ledger data items for use with, e.g., the system of FIG. 1.

An illustrative method 200 of using healthcare protocols to classify event data items as distributed ledger data items for use with, e.g., the illustrative system of FIG. 1, is depicted in FIG. 2. The method 200 includes providing healthcare protocols 202. Each healthcare protocol may be associated with, or correspond, to a health condition, and may include, among other things, a list of event data items that should be recorded in, or hashed to, a distributed ledger (e.g., event data items that should be made immutable) for a patient having the health condition associated with the healthcare protocol. Healthcare protocols may further include a care pathway (e.g., clinical pathway, integrated care pathway, care map, case management plan, etc.) for the associated health condition. Thus, care providers may use the care pathway contained within a healthcare protocol to provide care for a patient having health condition associated with the healthcare protocol. In other words, care providers may follow the care pathway of the healthcare protocol to treat a patient having a health condition associated with the healthcare protocol.

For example, the plurality of provided healthcare protocols 202 may include a lung cancer healthcare protocol. The lung cancer healthcare protocol may include a lung cancer care pathway and a list of event data items that should be recorded in a distributed ledger for patients who have lung cancer. A care provider such as a physician may consult the lung cancer healthcare protocol for the lung cancer care pathway so as to provide treatment for a patient having lung cancer (e.g., the lung cancer care pathway may include information with respect to the treatment of a patient having lung cancer). Further, the illustrative systems and methods described herein may consult the lung cancer healthcare protocol when receiving and handling health care events including event data items for patients having lung cancer as will be described below.

In other words, the illustrative systems and methods may include a plurality of healthcare protocols corresponding to a plurality of different health conditions. In some embodiments, the healthcare protocols may be assigned to patients having the associated health conditions by a care provider such as a physician.

Further, in some embodiments, the healthcare protocols may be assigned to patients having the associated health conditions by the illustrative systems and methods described herein. For example, the illustrative systems and methods may identify patients who may benefit by having particular healthcare protocols assigned to them based on data about such patients that is received from various participants. For instance, a participant may provide weight and height information for a patient, and based on the weight and height information, the illustrative systems and methods may automatically assign a weight loss healthcare protocol to the patient.

The method 200 may further include receiving a health care event 204. A healthcare event may be transmitted by a participant to, e.g., the illustrative system 100 of FIG. 1, and may include one or more event data items that are associated with the healthcare event. For example, a healthcare event may be blood drawn from a patient and laboratory-tested for a panel of diseases. Each result of each test on the tested blood may be an event data item for the healthcare event. Further for example, a healthcare event may be a provider decision event regarding the patient such as a drug dosage decision. One or more event data items of a drug dosage decision may include the drug dosage and one or more health factors of the patient related to the drug dosage. If the drug dosage is changed from a previous dosage, the previous dosage may also be an event data item of the drug dosage decision. Thus, each change would be logged in the distributed ledger as individual, trackable events. Other illustrative healthcare events may include weight, BMI, blood pressure, genetics, and device data (e.g., implantable medical device data such as from pacemakers, drug pumps, stimulators, etc.).

Upon reception of a healthcare event, the illustrative method 200 may identify one or more healthcare protocols 206 based on the received healthcare event, or more specifically, the patient associated with the received healthcare event. For instance, one of the data items of the healthcare event may a patient identification or a listener and receiver may assign patient identification to the healthcare event. The method 200 may use the patient identification to determine whether any healthcare protocols have been assigned to the patient. If there have been one or more healthcare protocols assigned to the patient, the method 200 may further use the assigned healthcare protocols to, e.g., determine what to do with the event data items of the received healthcare event. If there have not been one or more healthcare protocols assigned to the patient, the method 200 may simply not have any healthcare protocols to use with the received healthcare event and/or may attempt to automatically assign one or more healthcare protocols to the patient based on the event data items of the healthcare event as described herein.

The illustrative method 200 may further classify one or more event data items of the received healthcare event as distributed ledger data items 208 according to, or in accordance with, the identified one or more healthcare protocols. For example, the rules engine 105 of the processor and decider 104 of the system 100 of FIG. 1 may be used to classify the one or more event data items of the received healthcare event as distributed ledger data items 208 based on, or according to, the identified one or more healthcare protocols. Some healthcare protocols may have a longer, or larger, list of data items that should be recorded in the distributed ledger than other healthcare protocols. Thus, for example, depending on the identified healthcare protocols for a particular patient, more or less event data items of the healthcare event may be recorded in, or hashed to, the distributed ledger so as to be made immutable.

If event data items of the received healthcare event are determined to be distributed ledger data items, distributed ledger transaction requests may be generated for the distributed ledger data items 212, and such distributed ledger transaction requests may be submitted to a distributed ledger 214. Additionally, the healthcare event including all event data items as well as the distributed ledger data items and information with respect to the distributed ledger transactions may be stored in the off-ledger storage 210. One embodiment of these processes will be described herein in more detail with respect to FIGS. 3-4.

If no event data items of the received healthcare event are determined to be distributed ledger data items, the healthcare event including all event data items as well as reconciliation information why the event data items were not recorded in the distributed ledger may be stored in the off-ledger storage 210. One embodiment of these processes will be described herein in more detail with respect to FIG. 5.

Figure 3:
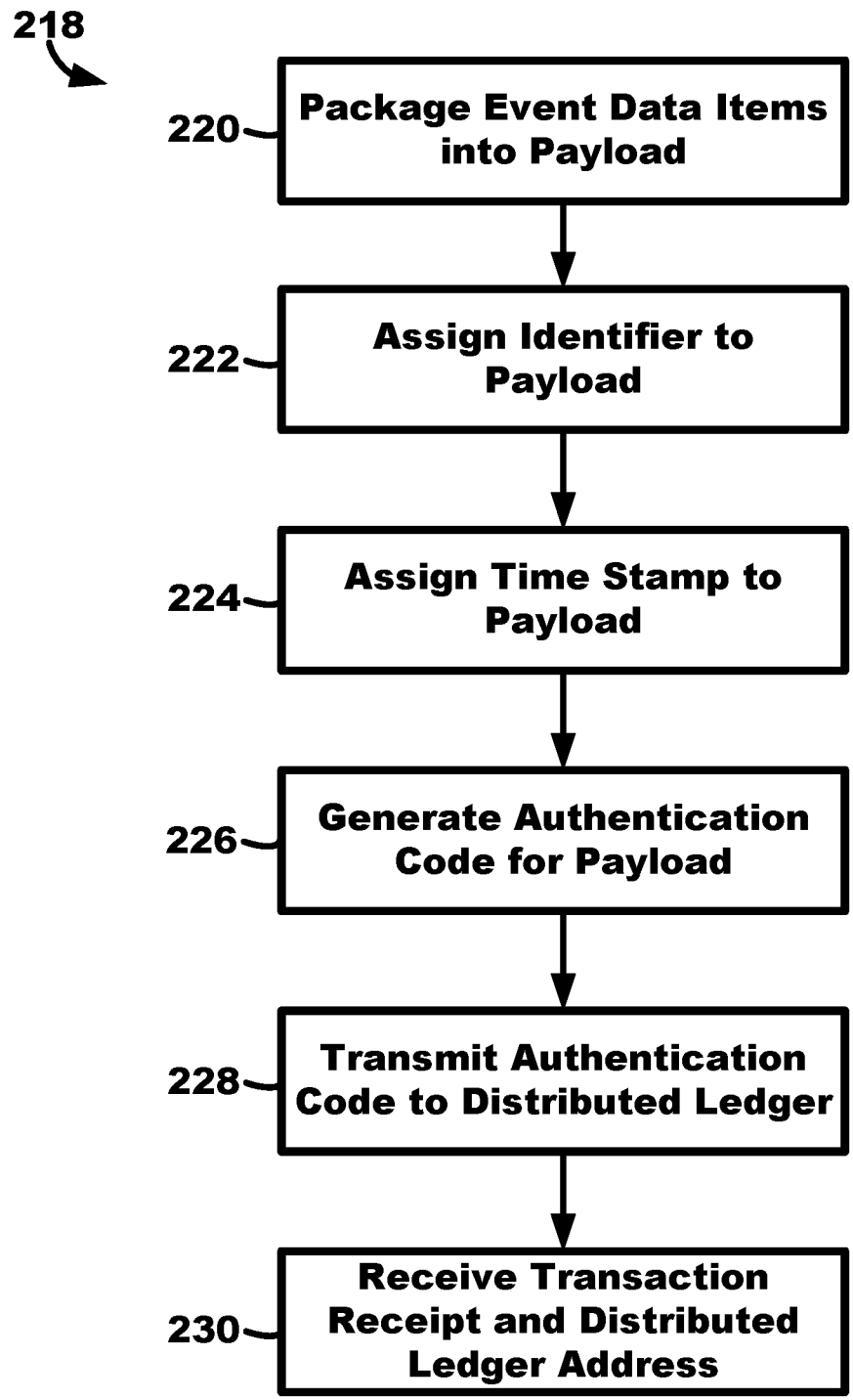
FIG. 3 is a flow diagram of an illustrative method of generating and submitting distributed ledger transaction requests for use with, e.g., the system and method of FIGS. 1-2.

An illustrative method 218 of generating and submitting distributed ledger transaction requests for use with, e.g., the illustrative system and method of FIGS. 1-2, is depicted in FIG. 3. The method 218 may be invoked, or initiated, when one or more event data items are classified as distributed ledger data items (e.g., when the one or more event data items are identified in a healthcare protocol as being distributed ledger items). Generally, the method 218 may initially generate a payload. A payload may be described as including any data the represents the information which is to be written to the off-ledger store and "hashed" to the distributed ledger. To generate the payload, the method 218 may include packaging the one or more event data items of a received healthcare event classified as distributed ledger data items into a payload 220, assigning an identifier to the payload 222, and assigning a time stamp to the payload 224. The time stamp may be defined as the period at which an action (e.g., an event, a trigger, data reception, a decision, etc.) of the healthcare event is noted.

Additionally, the method 218 may perform reconciliation (to, e.g., ensure proper versioning and change management of the rules engine that is leveraged) of the decision. In other words, a "double-check" may be performed at packaging to ensure that the proper healthcare protocol and proper rules engine were utilized.

Next, the method 218 may further include generating a keyed-hash message authentication code for (e.g., based on) the payload 226 and transmitting the keyed-hash message authentication code to the distributed ledger 228. The keyed-hash message authentication code (HMAC) may be generated using a cryptographic hash function with a "salt" (e.g., a secret key), and may be used to verify data integrity and the authentication of a message. After the keyed-hash message authentication code has been sent to the distributed ledger 228, the method 218 may wait to receive a transaction receipt and distributed ledger address from the distributed ledger after the keyed-hash message authentication code has been recorded on, or hashed to, the distributed ledger 230. The distributed ledger address may be the location of the transaction within the distributed ledger, which may be later used to recall the HMAC for use in verification processes as further described herein.

In other words, if a decision was made (e.g., classifying one or more event data items as distributed ledger data items), the data may be packaged, and a universally unique identifier (UUID) may be generated. Then, a time stamp (TS) may be obtained. An HMAC may be used to fingerprint the package to be stored on the distributed ledger (HMAC of PL+UUID+TS), and then the packaged data may be sent to the distributed ledger for consensus leveraging the distributed ledger consensus methods and distribution. Next, the process may wait for confirmation from the distributed ledger such as reception of a receipt notification from the distributed ledger that the transaction was completed. The receipt may be the transaction hash from the distributed ledger and the address of the transaction's location within the distributed ledger.

Figure 4:
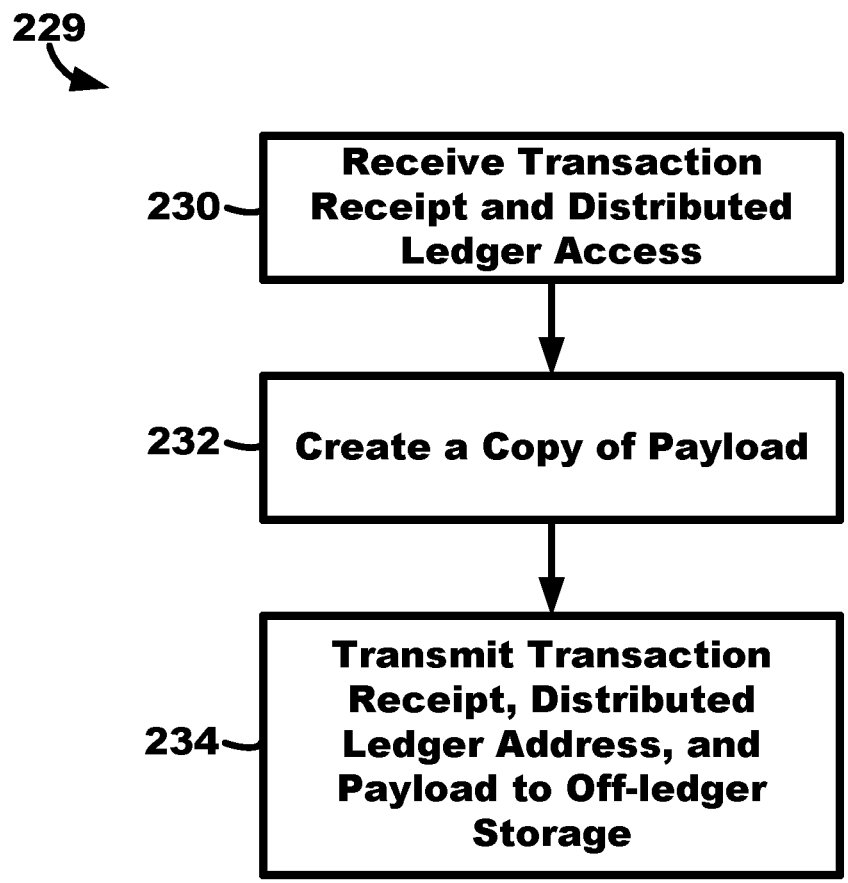
FIG. 4 is a flow diagram of an illustrative method of storing a healthcare event in off-ledger storage after submitting distributed ledger transaction requests related thereto for use with, e.g., the system and methods of FIGS. 1-3.

After the event data items classified as distributed ledger data items have been recorded to, or hashed to, the distributed ledger, such event data items as well as any other event data items and other data related to the healthcare event may be stored in the off-ledger storage. An illustrative method 229 of storing a healthcare event in off-ledger storage after submitting distributed ledger transaction requests related thereto for use with, e.g., the illustrative system and methods of FIGS. 1-3, is depicted in FIG. 4.

The method 228 may include receiving a transaction receipt and distributed ledger address (e.g., where the record of the payload is located in the distributed ledger) from the distributed ledger in response to recordation of the keyed-hash message authentication code 230, creating a copy of the payload including the identifier and time stamp for storage as a package 232, and transmitting the transaction receipt, the distributed ledger address, and the payload to the off-ledger storage for storage thereon.

In other words, a copy of the payload and a linkage for storage within, or on, the off-ledger storage may be generated. The linkage may point to the attribution record within the distributed ledger (e.g., a blockchain address). The response data from the distributed ledger such as the address and the transaction hash may then be used, and the TS and UUID may be appended to the payload as metadata of the completed work. A data package (such as, e.g., JSON object) may be generated and sent to the off-ledger storage for storage thereon. Thus, the packaged copy of the payload data may be written to and stored on the off-ledger storage.

Figure 5:
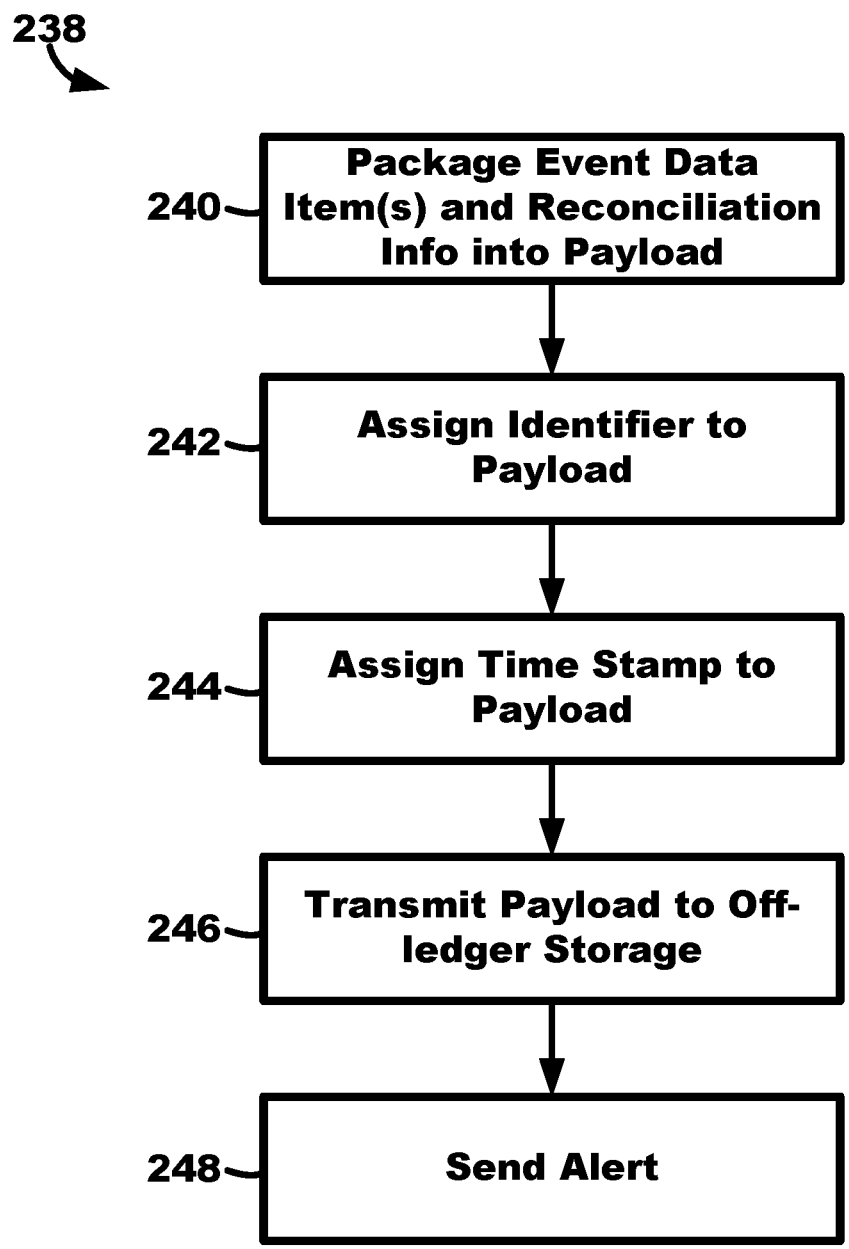
FIG. 5 is a flow diagram of an illustrative method of storing a healthcare event in off-ledger storage without submitting distributed ledger transaction requests related thereto for use with, e.g., the system and methods of FIGS. 1-4.

Further, if event data items were not classified as distributed ledger data items, and thus, not recorded to, or hashed to, the distributed ledger, such event data items as well as any other event data items and other data of the healthcare event may be stored in the off-ledger storage. An illustrative method 238 of storing a healthcare event in off-ledger storage without submitting distributed ledger transaction requests related thereto for use with, e.g., the illustrative system and methods of FIGS. 1-4, is depicted in FIG. 5. The method 238 may include packaging the event data items of the received healthcare event and reconciliation information in a payload 240.

The reconciliation information may include, among other things, why the event data items were not recorded in the distributed ledger. For example, the reconciliation information may include a copy of a portion of the healthcare protocol or a copy of the entire healthcare protocol being using to determine that the event data items are not to be classified as distributed ledger data items. Further, for example, the reconciliation information may include a copy of a portion of the rules engine or a copy of the entire rules engine that was used to determine that the event data items are not to be classified as distributed ledger data items. Still further, for example, the reconciliation information may include a version number or fingerprint of one or both of the healthcare protocol and rules engine that were used to determine that the event data items are not to be classified as distributed ledger data items.

Similar to as in the methods of FIGS. 3-4, an identifier may be assigned to the payload 242 and a time stamp may also be assigned to the payload 244. Then, the payload may be transmitted to the off-ledger storage for storage thereon 246. Lastly, the method 238 may further send, or provide, an alert, or message, 248 to a user (e.g., care provider) that the event data items were not classified as distributed ledger data items to be recorded in, or hashed to, the distributed ledger. Thus, a user may be given notice, and may, in some embodiments, be given the opportunity to override the healthcare protocol such that such event data items would be classified as distributed ledger data items, and then recorded in the distributed ledger. Additionally, the alert may also provide a potential opportunity for future review (e.g., to change the healthcare protocol, etc.). For example, a user or the system itself may take note of an alert and the respective healthcare protocol so as to analyze the healthcare protocol in the future and, if determined, make changes to the healthcare protocol based on such analysis.

In other words, if a decision was made to not classify the event data items as distributed ledger data items for recordation on the distributed ledger, the data may be packaged, and a timestamp, reconciliation of a non-decision, hash decision data, and any meta data may be appended to the package. The packaged data may then be sent to the off-ledger storage, and an alert may be sent indicating that a decision was made to not classify the event data items as distributed ledger data items.

Figure 6:
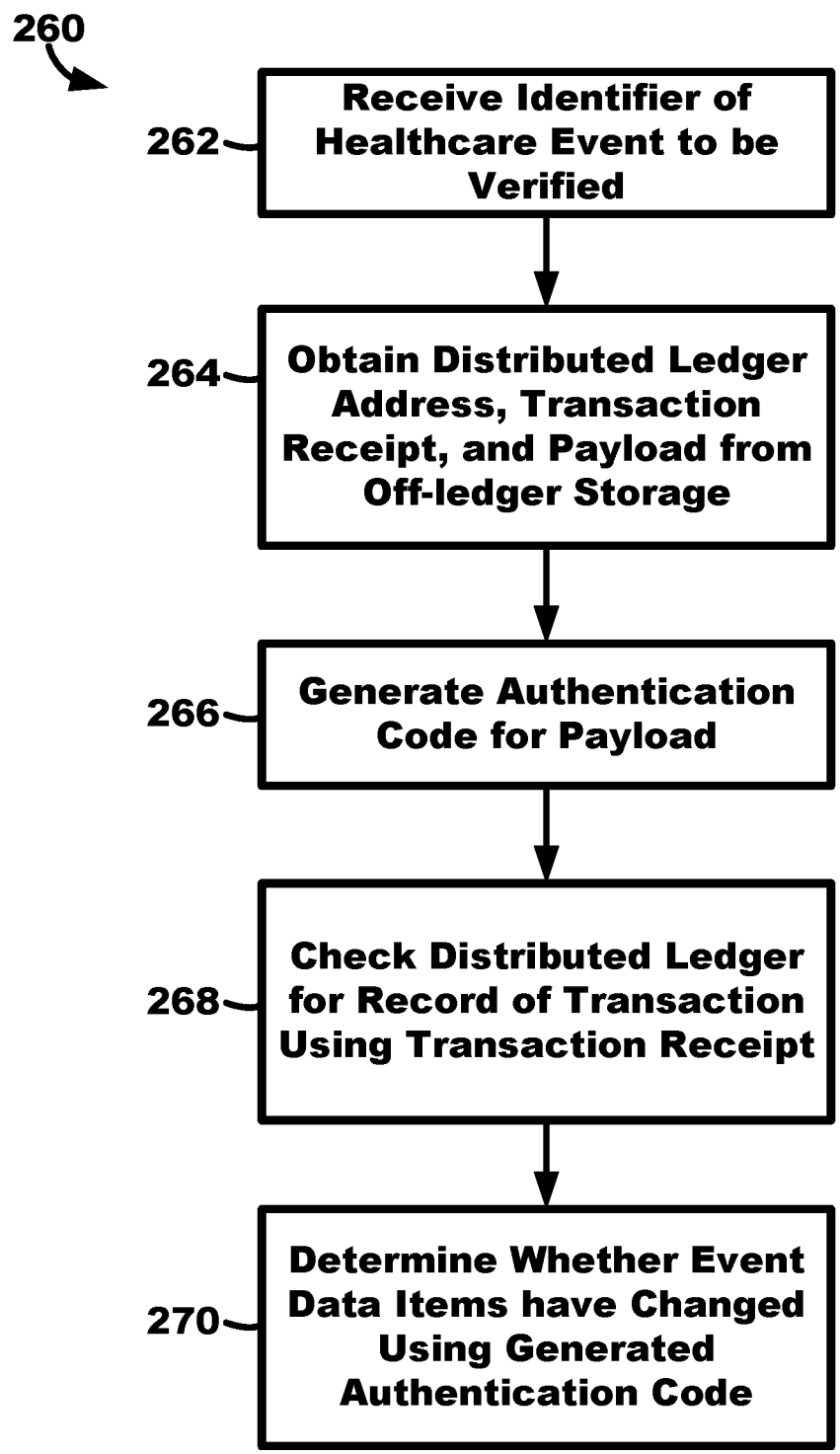
FIG. 6 is a flow diagram of an illustrative method of verifying a healthcare event using a distributed ledger and off-ledger storage for use with, e.g., the system and methods of FIGS. 1-5.

After event data items are recorded in, or hashed to, the distributed ledger, the distributed ledger may be used to verify the accuracy of the event data items as stored in the off-ledger storage. An illustrative method 260 of verifying event data items using a distributed ledger and off-ledger storage for use with, e.g., the illustrative system and methods of FIGS. 1-5, is depicted in FIG. 6. The method 260 may include receiving the identifier of the event data items to be verified 262. The identifier may then be used to obtain the distributed ledger address of the transaction, the transaction receipt, and the payload from the off-ledger storage 264, and a keyed-hash message authentication code for the payload may be generated 266. The transaction receipt from the off-ledger storage may be used to determine if a record of the transaction exists on the distributed ledger, and thus, the method 260 may include checking the distributed ledger for record of the transaction using the transaction receipt. If record of transaction exists in the distributed ledger, the method 260 may further include determining whether the event data items have changed by using the keyed-hash message authentication code generated from the payload in the off-ledger storage and the distributed ledger 270. In one or more embodiments, such determination may be accomplished by invoking a smart contract to ingest the keyed-hash message authentication code generated from the payload in the off-ledger storage and return a "pass" or "fail" message.

In other words, one component, or module, of the illustrative systems and methods described herein is a verification check to ensure that the distributed ledger and the off-ledger storage are consistent regarding the data each has captured. First, the off-ledger record to be verified may be obtained. For example, a UUID may be posted to an API, which will retrieve the distributed ledger transaction hash receipt, the distributed ledger address, the TS, and the payload content from off-ledger storage. Next, a HMAC may be generated from the payload. Then, the transaction hash receipt may be checked on the distributed ledger. For example, an API may use the transaction hash receipt and check the distributed ledger for its existence. If found, the API may query the distributed ledger for the transaction hash receipt's distributed ledger address (e.g., the smart contract), and compare it to the value provided from the off-ledger storage. If it is valid, the smart contract may be invoked by passing the UUID provided by requester, the HMAC generated by API, and the TS of the transaction. It is to be understood to one having ordinary skill in the art that this implementation may be considered to be a set of meta data components and may further be a configurable set. Also, this configuration may depend on the smart contract design and may further be subjective to the purpose of what is being recorded within the distributed ledger, defined by the participant, and in accordance with any changes over time. Invoking the smart contract will ingest the data provided and return a "pass" or "fail" message as it compares the HMAC within the content within the smart contract. If a "pass" message is returned, the API may return the off-ledger storage payload content that has been "verified" to match/be consistent to what is contained within the distributed ledger.

It is to be understood that there is a possibility that the off-ledger storage could be "tampered with" and orphaned content may exist on the distributed ledger, which may question the integrity of the system. To mitigate such issues, it is to be understood that the illustrative systems and methods may implement redundant, or another, distributed ledger solution to host copies of the data stored in the sources, add additional verification steps within the smart contract design (e.g., three steps to verify that UUIDs have not changed and the processes, or steps, were followed and written to the distributed ledger), and an elastic search tool to link, compare, and monitor distributed ledger and off-ledger addresses and UUIDs.

The healthcare protocols including, among other things, care pathways and lists of event data items that should be recorded in, or hashed to, a distributed ledger may be modified over time automatically through the illustrative systems and methods, automatically through other systems and methods, and/or manually by users. When these healthcare protocols change, such changes may be recorded in the distributed ledger so as to be made immutable. In this way, if a healthcare protocol has changed, it would be possible to determine when, how, and perhaps why, the healthcare protocol has changed.

Figure 7:
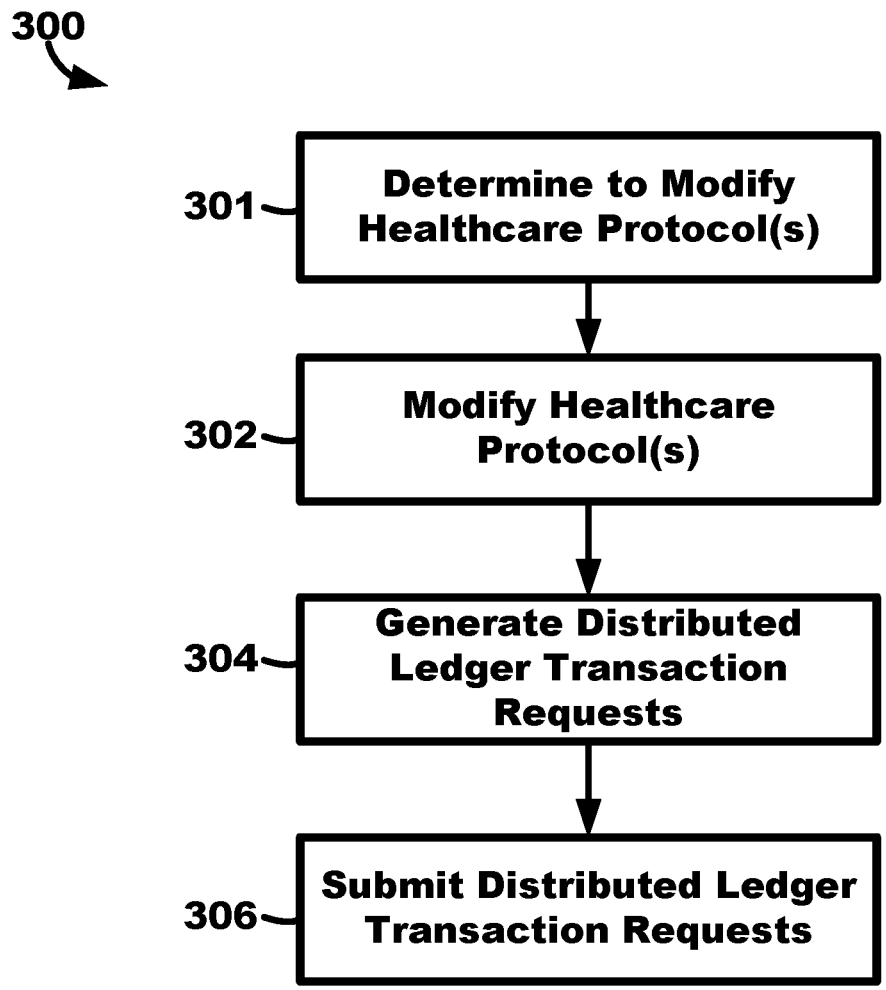
FIG. 7 is a flow diagram of an illustrative method of modifying a healthcare protocol and recording the modifications in a distributed ledger for use with, e.g., the system and methods of FIGS. 1-6.

An illustrative method 300 of modifying a healthcare protocol and storing the modifications in a distributed ledger for use with, e.g., the illustrative system and methods of FIGS. 1-6, is depicted in FIG. 7. The method 300 may include determining to modify a healthcare protocol 301, and if determined to do so, modifying a healthcare protocol 302. As described herein, the modification of the healthcare protocol can be performed automatically using various systems and methods. In one example, illustrative systems and methods may monitor and analyze a healthcare protocol by monitoring the data recorded in the distributed ledger for the healthcare protocol for one or more patients and by monitoring the data not recorded in the distributed ledger and only stored in the off-ledger storage for the healthcare protocol for one or more patients. The illustrative systems and methods may use such monitoring and analysis to determine whether the healthcare protocol should be changed 301. In one example, the healthcare outcomes resulting from a healthcare protocol may also be monitored, and if it is determined 301 that the monitored healthcare outcomes for the healthcare protocol can be improved, then the healthcare protocol may be modified in view thereof. For example, if a selected, or particular, healthcare protocol did not call for a specific patient test that may result in better healthcare outcomes, the care pathway of the healthcare protocol may be modified to the include the specific patient test. Further, for example, if a heart failure patient recently gains several pounds while properly maintaining their diet, then the care pathway of the healthcare protocol may be modified to increase the patient's diuretic, and the illustrative systems and methods may monitor and assess such results over one or more days for effectiveness. In other word, generally, any new event info coming into the distributed ledger may regularly be reviewed, which may potentially result in a recommended change to the specific care pathway of and/or any other portion of the healthcare protocol for that patient.

Further, the modification of the healthcare protocol 302 can be performed manually by a user, e.g., in review of data recorded in the distributed ledger for the healthcare protocol for one or more patients, data not recorded in the distributed ledger and only stored in the off-ledger storage for the healthcare protocol for one or more patients, and other data related to the healthcare protocol (such as, e.g., journal articles, published research, etc.).

Once a healthcare protocol has been modified, the method 300 may include generating distributed transaction requests for the modification 304, and then submitting the distributed transaction requests to the distributed ledger 306. Similar to the healthcare events and event data items described above, the healthcare protocol modifications can also be stored in the off-ledger storage, which may be verified against the distributed ledger to verify the accuracy of the healthcare protocol modifications.

Figure 8:
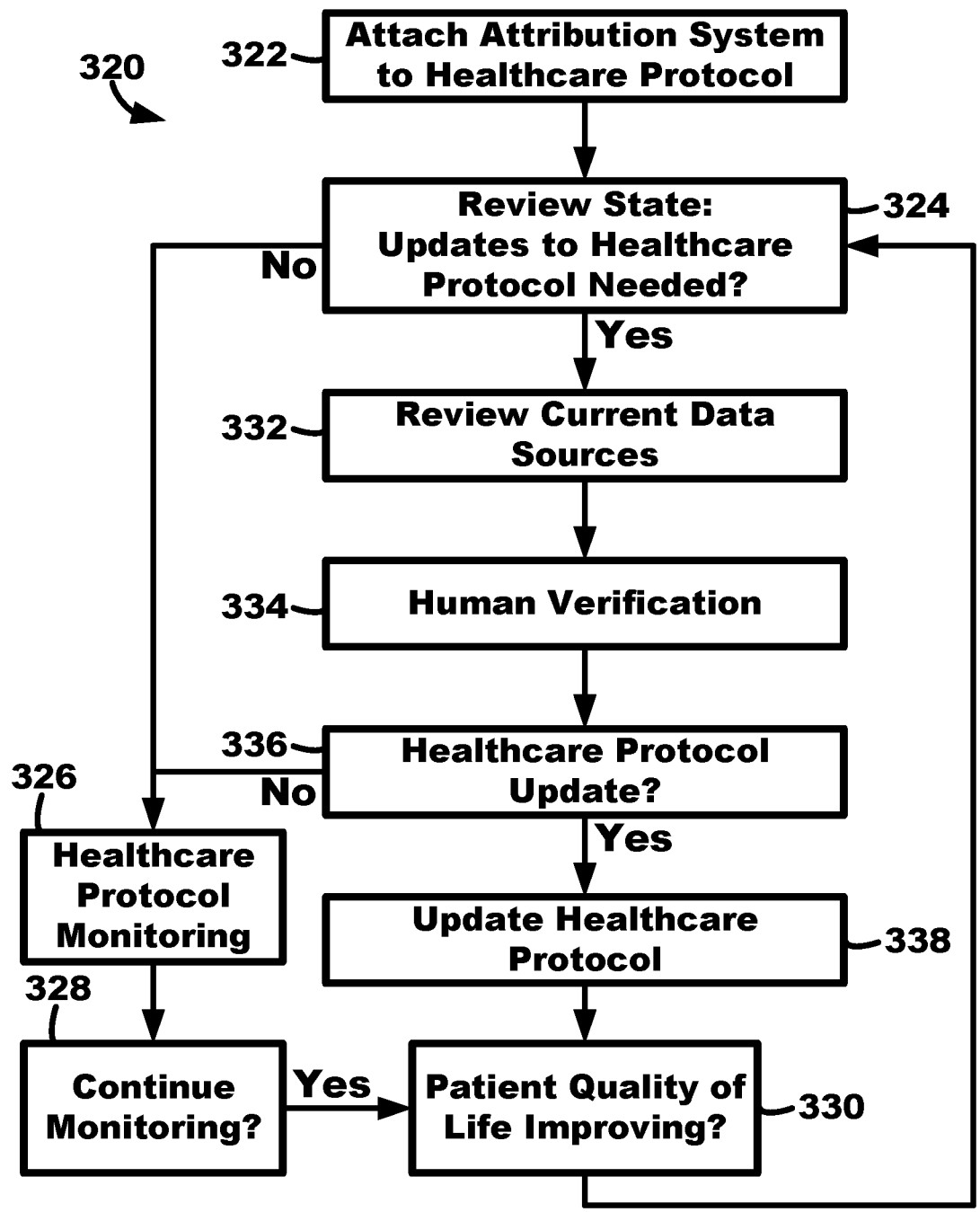
FIG. 8 is a flow diagram of an illustrative method of modifying a healthcare protocol for use with, e.g., the system and methods of FIGS. 1-7.

Modification of a healthcare protocol may include many "checks and balances" and analysis of various sources of data before any modification may take place. One illustrative method 320 of modifying a healthcare protocol for use with, e.g., the illustrative system and methods of FIGS. 1-7, is depicted in FIG. 8. The method 320 may include attaching an attribution system, such as system 100 including reporter 115 described herein with respect to FIG. 1, to a selected healthcare protocol (e.g., a lung cancer healthcare protocol) 322. The system may be configured to perform one or more of the remaining processes of method 320.

The state of the selected healthcare protocol may be reviewed; for example, are updates to the selected healthcare protocol already determined to be needed 324? If it is determined that updates to the selected healthcare protocol are not presently needed, the method 320 may monitor the selected healthcare protocol 326 by reviewing one or more various data sources such as, for example, any data recorded in the distributed ledger according to the selected healthcare protocol, any data stored in the off-ledger storage according to the selected healthcare protocol, any data received by other portions of the system that is related to the selected healthcare protocol, etc. In other words, data may be ingested from a variety of sources.

The data may be monitored, or ingested, for a period of time 328, and for example, periodically, it may be determined whether the data appears to indicate (e.g., based on patient outcomes, etc.) that the patients' quality of life is not improving 330. If it is determined that the patients' quality of life is not improving, the method 300 may return to reviewing the state of the selected healthcare protocol but now determining that the healthcare protocol should be changed or modified 324.

In one or more embodiments, when determining whether the patient's quality of life is not improving, the method 300 may use the rules engine to log payloads being recorded in the distributed ledger and report on such payloads for data mining and further algorithm development.

The method 300 may then include reviewing the data sources 332 such as, e.g., population health systems (which may be used to risk stratify a cohort), care management systems (which may be used to monitor cohort(s)), care pathway systems (which may be used to define a care protocols), other systems (e.g., any digital source such as a patient electronic medical records/electronic health records, lab results, scheduling, billing, etc.), and attribution system alerts (e.g., quality updates, data source updates, etc.).

The method 300 may then include human verification 334 of any findings and document the selected healthcare protocol changes or recommended changes. If it is determined to make a change to the selected healthcare protocol 336, then the method 300 may update the selected healthcare protocol 338 accordingly, and then return to determining whether the patients' quality of life is not improving 330. If the patients' quality of life is improving, the method 300 may end.

If it is not determined to make a change to the selected healthcare protocol 336, then the method 300 may return to treatment protocol monitoring 326 for a selected period of time. If it is determined to stop monitoring 328, the method 300 may end.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A system for use with a plurality of participants and a distributed ledger system including a set of ledger clients, each ledger client having a copy of a distributed ledger and configured to maintain the distributed ledger, the system separate from the distributed ledger system and comprising:
  a decider apparatus comprising one or more processors, the decider apparatus configured to:
    receive a healthcare event associated with a patient from one or more participants, the healthcare event comprising one or more event data items;
    identify, for the received healthcare event, one or more healthcare protocols associated with the patient corresponding to the received healthcare event;
    classify, based on the identified one or more healthcare protocols, one or more event data items of the received healthcare event as distributed ledger data items for recordation on the distributed ledger of the distributed ledger system;
    generate, for the one or more event data items of the received healthcare event classified as distributed ledger data items for recordation on the distributed ledger of the distributed ledger system, one or more distributed ledger transaction requests; and
    submit the one or more distributed ledger transaction requests to the distributed ledger system for recordation on the distributed ledger that were generated for the one or more event data items of the received healthcare event classified as distributed ledger data items for recordation on the distributed ledger of the distributed ledger system.

2. The system of claim 1, wherein the healthcare event comprises a provider decision event regarding the patient.

3. The system of claim 2, wherein the provider decision event comprises a drug dosage decision, wherein the one or more event data items of the drug dosage decision comprises:
  the drug dosage; and
  one or more health factors of the patient related to the drug dosage.

4. The system of claim 1, wherein the healthcare event comprises a testing event regarding the patient, wherein the one or more event data items of the testing event comprises laboratory test results.

5. The system of claim 1, wherein the one or more healthcare protocols associated with the patient corresponds to health conditions of the patient.

6. The system of claim 1, wherein the decider apparatus is further configured to allow a user to assign one or more healthcare protocols to the patient.

7. The system of claim 1, wherein the decider apparatus is further configured to:
  modify the one or more healthcare protocols; and
  generate, for the modified one or more healthcare protocols, one or more distributed ledger transaction requests.

8. The system of claim 7, wherein modifying the one or more healthcare protocols comprises modifying the one or more event data items to be classified as distributed ledger data items according to the one or more healthcare protocols.

9. The system of claim 8, wherein modifying the one or more event data items to be classified as distributed ledger data items according to the one or more healthcare protocols comprises allowing a user to modify the one or more event data items to be classified as distributed ledger data items according to the one or more healthcare protocols.

10. The system of claim 7, wherein modifying the one or more healthcare protocols comprises modifying the one or more healthcare protocols based on one or more patient outcomes using the one or more healthcare protocols.

11. The system of claim 1, wherein the one or more participants comprises one or more of patient monitoring apparatus, treatment data sources, payor systems, healthcare attribution coordinator systems, and provider systems.

12. The system of claim 1 further comprising off-ledger storage operably coupled to the decider apparatus, wherein the decider apparatus is further configured to:
  store the one or more event data items of the received healthcare event on the off-ledger storage; and
  determine whether the stored one or more event data items of the received healthcare event on the off-ledger storage that had been classified as distributed ledger items have been modified based on the distributed ledger.

13. The system of claim 1, wherein generating, for the one or more event data items of the received healthcare event classified as distributed ledger data items, one or more distributed ledger transaction requests comprises:
  packaging the one or more event data items of the received healthcare event classified as distributed ledger data items into a payload;
  assigning an identifier to the payload;
  assigning a time stamp to the payload;
  generating a keyed-hash message authentication code for the payload; and
  transmitting the keyed-hash message authentication code to the distributed ledger.

14. A method for use with a plurality of participants and a distributed ledger system including a set of ledger clients, each ledger client having a copy of a distributed ledger and configured to maintain the distributed ledger, the method executed by a system separate from the distributed ledger system and comprising:
  receiving a healthcare event associated with a patient from one or more participants, the healthcare event comprising one or more event data items;
  identifying, for the received healthcare event, one or more healthcare protocols associated with the patient corresponding to the received healthcare event;
  classifying, based on the identified one or more healthcare protocols, one or more event data items of the received healthcare event as distributed ledger data items for recordation on the distributed ledger of the distributed ledger system;
  generating, for the one or more event data items of the received healthcare event classified as distributed ledger data items for recordation on the distributed ledger of the distributed ledger system, one or more distributed ledger transaction requests; and
  submitting the one or more distributed ledger transaction requests to the distributed ledger system for recordation on the distributed ledger that were generated for the one or more event data items of the received healthcare event classified as distributed ledger data items for recordation on the distributed ledger of the distributed ledger system.

15. The method of claim 14, wherein the healthcare event comprises a provider decision event regarding the patient.

16. The method of claim 15, wherein the provider decision event comprises a drug dosage decision, wherein the one or more event data items of the drug dosage decision comprises:
  the drug dosage; and
  one or more health factors of the patient related to the drug dosage.

17. The method of claim 14, wherein the healthcare event comprises a testing event regarding the patient, wherein the one or more event data items of the testing event comprises laboratory test results.

18. The method of claim 14, wherein the one or more healthcare protocols associated with the patient corresponds to health conditions of the patient.

19. The method of claim 14, wherein the method further comprises allowing a user to assign one or more healthcare protocols to the patient.

20. The method of claim 14, wherein the method further comprises:
   modifying the one or more healthcare protocols; and
   generating, for the modified one or more healthcare protocols, one or more distributed ledger transaction requests.

21. The method of claim 20, wherein modifying the one or more healthcare protocols comprises modifying the one or more event data items to be classified as distributed ledger data items according to the one or more healthcare protocols.

22. The method of claim 21, wherein modifying the one or more event data items to be classified as distributed ledger data items according to the one or more healthcare protocols comprises allowing a user to modify the one or more event data items to be classified as distributed ledger data items according to the one or more healthcare protocols.

23. The method of claim 20, wherein modifying the one or more healthcare protocols comprises modifying the one or more healthcare protocols based on one or more patient outcomes using the one or more healthcare protocols.

24. The method of claim 14, wherein the one or more participants comprises one or more of patient monitoring apparatus, treatment data sources, payor systems, healthcare attribution coordinator systems, and provider systems.

25. The method of claim 14, wherein the method further comprises:
   storing the one or more event data items of the received healthcare event on off-ledger storage; and
   determining whether the stored one or more event data items of the received healthcare event on the off-ledger storage that had been classified as distributed ledger items have been modified based on the distributed ledger.

26. The method of claim 14, wherein generating, for the one or more event data items of the received healthcare event classified as distributed ledger data items, one or more distributed ledger transaction requests comprises:
   packaging the one or more event data items of the received healthcare event classified as distributed ledger data items into a payload;
   assigning an identifier to the payload;
   assigning a time stamp to the payload;
   generating a keyed-hash message authentication code for the payload; and
   transmitting the keyed-hash message authentication code to the distributed ledger.

27. A system for use with a plurality of participants and a distributed ledger system including a set of ledger clients, each ledger client having a copy of a distributed ledger and configured to maintain the distributed ledger, the system separate from the distributed ledger system and comprising:
   a decider apparatus comprising one or more processors, the decider apparatus configured to:
      provide one or more healthcare protocols used to classify event data items of healthcare events as distributed ledger data items to be recorded on the distributed ledger of the distributed ledger system;
      modify the one or more healthcare protocols;
      generate, for the modified one or more healthcare protocols, one or more distributed ledger transaction requests for recordation on the distributed ledger of the distributed ledger system; and
      submit the one or more distributed ledger transaction requests to the distributed ledger system for recordation on the distributed ledger.

28. The system of claim 27, wherein modifying the one or more healthcare protocols comprises modifying the one or more event data items to be classified as distributed ledger data items according to the one or more healthcare protocols.

29. The system of claim 28, wherein modifying the one or more event data items to be classified as distributed ledger data items according to the one or more healthcare protocols comprises allowing a user to modify the one or more event data items to be classified as distributed ledger data items according to the one or more healthcare protocols.

30. The system of claim 27, wherein modifying the one or more healthcare protocols comprises modifying the one or more healthcare protocols based on one or more patient outcomes using the one or more healthcare protocols.

31. The system of claim 27, wherein the healthcare events comprise one or more of a provider decision event regarding the patient and a testing event regarding the patient comprising laboratory test results.

32. A method for use with a plurality of participants and a distributed ledger system including a set of ledger clients, each ledger client having a copy of a distributed ledger and configured to maintain the distributed ledger, the method executed by a system separate from the distributed ledger system and comprising:
   providing one or more healthcare protocols used to classify event data items of healthcare events as distributed ledger data items to be recorded on the distributed ledger of the distributed ledger system;
   modifying the one or more healthcare protocols;
   generating, for the modified one or more healthcare protocols, one or more distributed ledger transaction requests for recordation on the distributed ledger of the distributed ledger system; and
   submitting the one or more distributed ledger transaction requests to the distributed ledger system for recordation on the distributed ledger.

33. The method of claim 32, wherein modifying the one or more healthcare protocols comprises modifying the one or more event data items to be classified as distributed ledger data items according to the one or more healthcare protocols.

34. The method of claim 33, wherein modifying the one or more event data items to be classified as distributed ledger data items according to the one or more healthcare protocols comprises allowing a user to modify the one or more event data items to be classified as distributed ledger data items according to the one or more healthcare protocols.

35. The method of claim 32, wherein modifying the one or more healthcare protocols comprises modifying the one or more healthcare protocols based on one or more patient outcomes using the one or more healthcare protocols.

36. The method of claim 32, wherein the healthcare events comprise one or more of a provider decision event regarding the patient and a testing event regarding the patient comprising laboratory test results.

* * * * *